US008664341B2

(12) United States Patent
Hefner, Jr.

(10) Patent No.: US 8,664,341 B2
(45) Date of Patent: *Mar. 4, 2014

(54) VINYLBENZYL ETHERS OF POLYCYCLOPENTADIENE POLYPHENOL

(75) Inventor: Robert E. Hefner, Jr., Rosharon, TX (US)

(73) Assignee: Dow Global Technologies, LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/643,656

(22) PCT Filed: Apr. 21, 2011

(86) PCT No.: PCT/US2011/000709
§ 371 (c)(1),
(2), (4) Date: Nov. 12, 2012

(87) PCT Pub. No.: WO2011/136845
PCT Pub. Date: Nov. 3, 2011

(65) Prior Publication Data
US 2013/0211015 A1    Aug. 15, 2013

Related U.S. Application Data

(60) Provisional application No. 61/329,356, filed on Apr. 29, 2010.

(51) Int. Cl.
C08F 290/06      (2006.01)
C08G 8/20        (2006.01)

(52) U.S. Cl.
USPC ........................................................ 525/502

(58) Field of Classification Search
USPC ........................................................ 525/502
See application file for complete search history.

(56) References Cited

U.S. PATENT DOCUMENTS

| | | | |
|---|---|---|---|
| 3,419,624 A | 12/1968 | Cotter et al. | |
| 4,456,129 A | 6/1984 | Baber | |
| 4,540,829 A | 9/1985 | Hefner, Jr. | |
| 4,546,131 A | 10/1985 | Hefner, Jr. | |
| 4,611,022 A | 9/1986 | Hefner, Jr. | |
| 4,629,762 A | 12/1986 | Hefner, Jr. | |
| 4,629,763 A | 12/1986 | Hefner, Jr. | |
| 4,629,764 A | 12/1986 | Hefner, Jr. | |
| 4,661,553 A | 4/1987 | Hefner, Jr. | |
| 4,707,533 A | 11/1987 | Hefner, Jr. | |

(Continued)

FOREIGN PATENT DOCUMENTS

| | | |
|---|---|---|
| EP | 0315089 | 5/1989 |
| GB | 1009019 | 11/1965 |

(Continued)

OTHER PUBLICATIONS

International Search Report and Written Opinion from related PCT application PCT/US2011/000709 dated Jul. 15, 2011, 12 pages.

International Preliminary Report on Patentability from related PCT application PCT/US2011/000709 dated Jul. 27, 2012, 7 pages.

Longoni, et al. "Hydroformylation and hydrocaronylation of dicyclopentadiene with cobalt-rhodium catalytic systems promoted by truphenylphosphine: Synthesis of monoformyltricyclodecenes, diformyltricyclodecanes and di (tricyclodecenyl) ketones", Molecular Catalysis 68, (1991), 7-21.

(Continued)

*Primary Examiner* — Mike M Dollinger
(74) *Attorney, Agent, or Firm* — Brooks, Cameron & Huebsch, PLLC

(57) ABSTRACT

Embodiments include vinylbenzyl ethers of polycyclopentadiene polyphenol that can be obtained by reacting a polycyclopentadiene polyphenol with a vinylbenzyl halide. Embodiments also include thermosettable compositions including the vinylbenzyl ethers of a polycyclopentadiene polyphenol and products obtained by curing the thermosettable compositions. Formula (I).

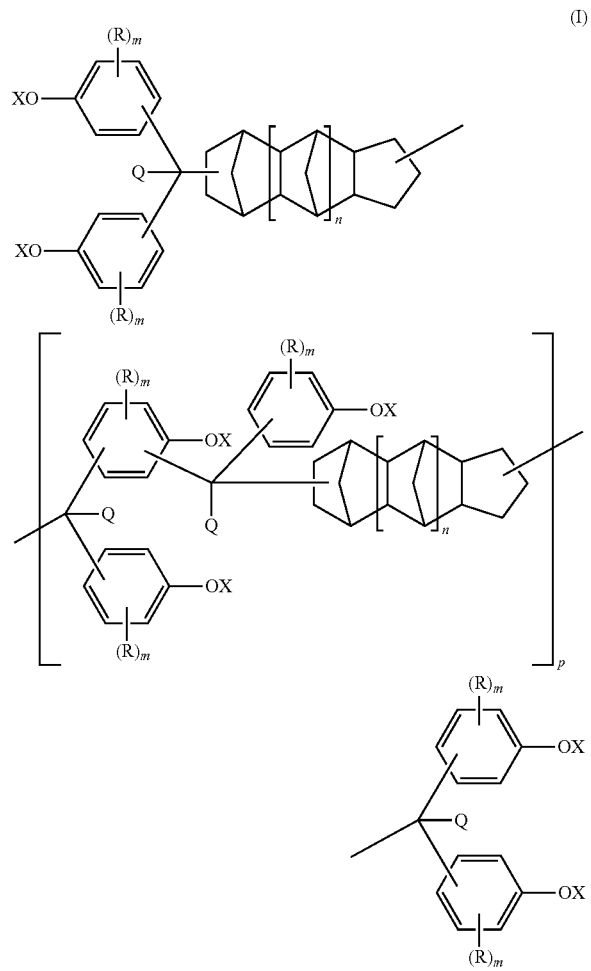

13 Claims, No Drawings

(56) References Cited

U.S. PATENT DOCUMENTS

| | | | |
|---|---|---|---|
| 4,766,184 | A | 8/1988 | Hefner, Jr. |
| 4,782,124 | A | 11/1988 | Hefner, Jr. et al. |
| 4,871,831 | A * | 10/1989 | Zweig et al. ............... 528/205 |
| 5,077,380 | A | 12/1991 | Hefner, Jr. et al. |
| 5,138,101 | A * | 8/1992 | Devon ............... 568/492 |
| 5,159,030 | A | 10/1992 | Hefner, Jr. |
| 5,206,321 | A | 4/1993 | Hefner, Jr. et al. |
| 5,281,675 | A | 1/1994 | Hefner, Jr. et al. |
| 5,428,125 | A | 6/1995 | Hefner, Jr. et al. |
| 5,442,039 | A | 8/1995 | Hefner, Jr. et al. |
| 5,602,211 | A | 2/1997 | Hefner, Jr. et al. |
| 6,307,108 | B1 | 10/2001 | Argyropoulos et al. |
| 7,321,068 | B2 | 1/2008 | Papp et al. |
| 2010/0189706 | A1 | 7/2010 | Chang et al. |
| 2011/0009559 | A1* | 1/2011 | Mullins et al. ............... 524/589 |
| 2011/0009560 | A1* | 1/2011 | Hefner et al. ............... 524/590 |
| 2011/0009562 | A1 | 1/2011 | Mullins et al. |
| 2011/0040046 | A1 | 2/2011 | Hefner, Jr. et al. |
| 2011/0046321 | A1 | 2/2011 | Earls et al. |
| 2012/0238668 | A1 | 9/2012 | Metral et al. |
| 2012/0238709 | A1 | 9/2012 | Metral et al. |
| 2012/0289663 | A1 | 11/2012 | Mullins et al. |

FOREIGN PATENT DOCUMENTS

| | | | |
|---|---|---|---|
| WO | 8905318 | 6/1989 | |
| WO | 2009114465 | 9/2009 | |
| WO | 2009114466 | 9/2009 | |
| WO | WO 2009114465 A1 * | 9/2009 | ............ C07C 261/02 |
| WO | WO 2009114466 A1 * | 9/2009 | ............ C07C 39/17 |

OTHER PUBLICATIONS

Kirk-Othmer, Encyclopedia of Chemical Technology, 5th ed., vol. 10, (2010), 347-470.

Kirk-Othmer, Encyclopedia of Chemical Technology, 5th ed., vol. 8, (2010), p. 219-235.

Muthyala, et al. "Bridged bicyclic cores containing a 1,1-diarylethylene motif are high-affinity subtype-selective ligands for the estrogen receptor", American Chemical Society, Journal of Medicinal Chemistry (2003), 46(9), 1589-1602.

Lekishvili, et al. "Polymers with organic-inorganic chains for the light-valve projection", Soobshcheniya Akademii Nauk Gruzinskoi SSR (1980), 98(1), 85-88.

H.E. Lee and K. Neville, "Handbook of Epoxy Resins", McGraw-Hill, New York, 1967, chapter 2, pp. 2-1 through 2-33.

Paquin, "Epoxidverbindungen und Epoxidharze", Springer-Verlag, Berlin, 1958, chapter 5, 131 pages.

Byrne, et al. "Magnesium-Oppenauer Oxidation of Alcohols to Aldehydes and Ketones", Tetrahedron Letters, vol. 28, No. 7, 1987, pp. 769-772.

Itsuno, et al. "Reaction of Aldehyde O-Alkyl Oxime with Organometallic Compounds", Tetrahedron Letters, vol. 27, No. 26, 1986, 3033-3036.

Hirao, et al. "Versatile Synthesis of ab-acetylenic ketones by oxidative nucleophilic addition of vanadium acetylides", Tetrahedron Letters, No. 27, No. 8, 1986, pp. 933 and 934.

Adlington, et al. "Azo Anions in Synthesis t-Butylhydrazones as Acyl-anion Equivalents", Journal of the Chemical Society: Chemical Communications, 1983, 1040-1041.

Martin and Bauer "Cyanic Acid Esters From Phenols: Phenyl Cyanate", Organic Synthesis, vol. 61, 1983, pp. 35-68.

Hwang, et al. "Dielectric behavior and properties of a cyanate ester containing dicyclopentadiene 1", Journal of Appiled Polymer Science, vol. 96, No. 6, 2005, pp. 2079-2089.

Green, et al. "Protective Groups in Organic Synthesis", Wiley-Interscience, New York, 1999, 67-74, 708-711.

Krompiec, et al. "Isomerization of allyl aryl ethers to their 1-propenyl derivatives catalysed by ruthenium complexes" Journal of Molecular Catalysis A: Chemical vol. 219, issue 1, 2004, 29-40.

Encyclopedia of Polymer Science and Technology, "Plastics, Resins, Rubbers, Fibers", vol. 1, 1964, 750-807.

Mukherjee, et al., "Pharmacophore mapping of selective binding affinity of estrogen modulators through classical and space modeling approaches: exploration of bridged-cyclic compounds with diarylethylene linkage", Journal of Chemical Information and Modeling (2007), 47(2), 475-487.

* cited by examiner

VINYLBENZYL ETHERS OF POLYCYCLOPENTADIENE POLYPHENOL

This application is a National Stage application under 35 U.S.C. 371 of PCT/US2011/000709, filed on Apr. 21, 2011 and published as WO2011/136845 A1 on Nov. 3, 2011, which claims the benefit of U.S. Provisional Application Ser. No. 61/329,356 filed Apr. 29, 2010, the entire contents of which are incorporated herein by reference in its entirety.

FIELD OF DISCLOSURE

This disclosure relates to thermosettable monomers, and in particular vinylbenzyl ethers of polycyclopentadiene polyphenol.

BACKGROUND

Thermosettable monomers are compounds that can be crosslinked. Crosslinking, also referred to as curing, converts the thermosettable monomers, which have a relatively low molecular weight, into crosslinked polymers, which have a relatively high molecular weight, by chemical reaction. Some of these crosslinked polymers, which can be said to be thermoset, can soften when heated, but do not melt or flow.

Many types of thermosettable monomers and crosslinked polymers are available. Thermosettable monomers can be purchased as pellets, powders, granules, or liquids. Alternatively, thermosettable monomers that have undergone partial curing can be purchased in stock shapes such as bars, sheets, and films.

Thermosettable monomers and crosslinked polymers can be based on a variety of chemistries. Examples of these chemistries include epoxy resins, polycyanates, polyacrylates, polyureas, and polyurethanes.

Some properties of thermosettable monomers and crosslinked polymers that can be considered for particular applications include mechanical properties, thermal properties, electrical properties, optical properties, processing properties, and physical properties. Mechanical properties can include flexural strength, tear strength, tensile strength, yield strength, tensile modulus, elongation, and impact toughness. Thermal properties can include maximum use temperature, deflection temperature, glass transition temperature, thermal conductivity, and coefficient of thermal expansion. Electrical and optical properties can include electrical resistivity, dielectric strength, dielectric constant or relative permittivity, index of refraction, and light transmission. Processing and physical properties can include bulk or apparent density, water absorption, viscosity, process temperature, shrinkage, and melt flow index.

SUMMARY

For the various embodiments, the vinylbenzyl ethers of polycyclopentadiene polyphenol are represented by the following Formula I:

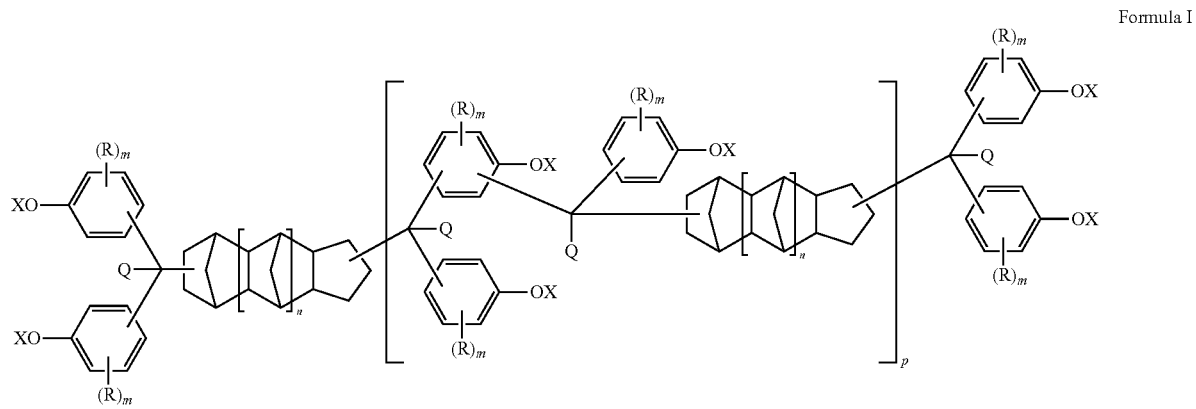

Formula I in which each n independently has a value from zero to 20; each m independently has a value of zero to 3; p has a value of zero to 20; each R is independently a halogen, a nitrile group, a nitro group, an alkyl group, an alkoxy group, an alkenyl group, or an alkenyloxy group, where the alkyl group, the alkoxy group, the alkenyl group, and the alkenyloxy group each independently contain 1 to 6 carbon atoms; each Q is independently hydrogen or an alkyl group containing 1 to 6 carbon atoms; and each X is a group of Formula II

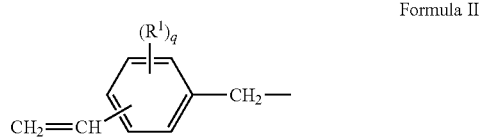

Formula II in which each $R^1$ is independently a halogen, a nitrile group, a nitro group, an alkyl group, an alkoxy group, an alkenyl group, or an alkenyloxy group, where the alkyl group, the alkoxy group, the alkenyl group, and the alkenyloxy group each independently contain 1 to 6 carbon atoms; and each q independently has a value of zero to 4.

Embodiments of the present disclosure also include a thermosettable composition that includes the vinylbenzyl ethers of polycyclopentadiene polyphenol represented by Formula I. Embodiments of the present disclosure also include thermosettable compositions including a comonomer. Embodiments of the present disclosure also include products that are obtainable by curing the thermosettable compositions including the vinylbenzyl ethers of polycyclopentadiene polyphenol represented by Formula I.

The above summary of the present disclosure is not intended to describe each disclosed embodiment or every implementation of the present disclosure. The description that follows more particularly exemplifies illustrative embodiments.

DETAILED DESCRIPTION

Embodiments of the present disclosure provide vinylbenzyl ethers of polycyclopentadiene polyphenol. The vinylbenzyl ethers of polycyclopentadiene polyphenol of the present disclosure can provide a high functionality, herein being at least four functional groups per molecule, which can help provide properties that are desirable for some applications.

The vinylbenzyl ethers of polycyclopentadiene polyphenol can be included in a thermosettable composition. Herein, a composition can be single-component or multi-component. For one or more embodiments, the thermosettable composition is cured to form a homopolymer. For one or more embodiments, the thermosettable composition is cured to form a copolymer. Themosettable compositions that include the vinylbenzyl ethers of polycyclopentadiene polyphenol can provide a relatively lower cure enthalpy and more rapid onset to uncatalyzed cure without depressing glass transition temperature, as compared some other compositions such as some polycyanate compositions. This relatively lower cure enthalpy can help to control exothermic chemical reactions that occur during curing and require less energy for curing Additionally, the relatively lower cure enthalpy can help prevent material decomposition, defect formation, and/or damage to manufacturing equipment that can occur with the relatively greater peak cure enthalpies.

Products that are obtained by curing the thermosettable compositions disclosed herein can have a greater glass transition temperature as compared to products obtained by curing other compositions such as some polycyanate compositions.

For the various embodiments, the vinylbenzyl ethers of polycyclopentadiene polyphenol are represented by the following Formula I:

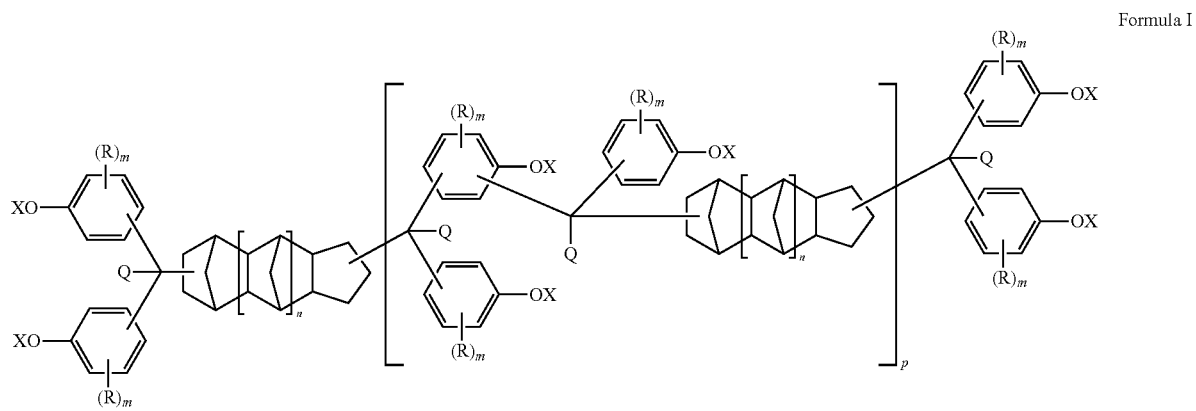

Formula I in which each n independently has a value from zero to 20; each m independently has a value of zero to 3; p has a value of zero to 20; each R is independently a halogen, a nitrile group, a nitro group, an alkyl group, an alkoxy group, an alkenyl group, or an alkenyloxy group, where the alkyl group, the alkoxy group, the alkenyl group, and the alkenyloxy group each independently contain 1 to 6 carbon atoms; each Q is independently hydrogen or an alkyl group containing 1 to 6 carbon atoms; and each X is a group of Formula II

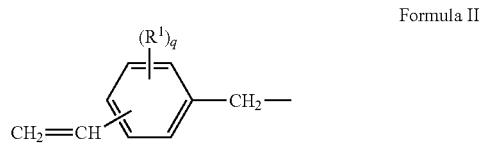

Formula II in which each $R^1$ is independently a halogen, a nitrile group, a nitro group, an alkyl group, an alkoxy group, an alkenyl group, or an alkenyloxy group, where the alkyl group, the alkoxy group, the alkenyl group, and the alkenyloxy group each independently contain 1 to 6 carbon atoms; and each q independently has a value of zero to 4.

For one or more embodiments, each R halogen and each $R^1$ halogen is independently selected from the group of fluorine, chlorine, and bromine. As discussed herein, each n can independently have a value from zero to 20. Preferably, each n can independently have a value from zero to 3, and most preferably each n can independently have a value from zero to 2. Preferably, p has a value from zero to 3, more preferably p has a value from zero to 2, and most preferably p has a value from zero to 1.

For one or more embodiments that include an alkyl group, preferably, each alkyl group can independently contain 1 to 2 carbon atoms. For one or more embodiments that include an alkoxy group, preferably, each alkoxy group can independently contain 1 to 2 carbon atoms. For one or more embodiments that include an alkyl group and/or an alkoxy group, preferably, the alkyl group and/or the alkoxy group are unsubstituted. For the various embodiments, when Q is an alkyl group it can preferably contain 1 to 2 carbon atoms.

The disclosed vinylbenzyl ethers of polycyclopentadiene polyphenol can be obtained by reacting polycyclopentadiene polyphenol, with a stoichiometric excess of a vinylbenzyl halide per phenolic hydroxyl group in the presence of a stoichiometric excess of a base compound per phenolic hydroxyl group and in the presence of a solvent.

Polycyclopentadiene polyphenols can be produced from polycyclopentadiene dialdehydes. As used herein, the prefix "poly" means that a compound has two or more of a particular moiety. "Compound" refers to a substance composed of atoms or ions of two or more elements in chemical combination. For example, a cyclopentadiene compound having two cyclopentadiene moieties (dicyclopentadiene) is a specific polycyclopentadiene. Polycyclopentadiene dialdehydes can be produced via hydroformylation of polycyclopentadiene, such as, dicyclopentadiene using syngas, a phosphine ligand, and a transition metal (from Groups 3 through 10) catalyst using a method such as described by G. Longoni, et al, J. of Molecular Catalysis 68, 7-21 (1991) or more generally in Kirk-Othmer, ENCYCLOPEDIA OF CHEMICAL TECHNOLOGY, Fifth Edition, Vol. 10, pp. 347-470 (2010). There can be variations in this process. For example, a method as described in U.S. Pat. No. 6,307,108 uses mixed polar/nonpolar solvents to ease the problem of catalyst recycle and product separation. The resulting polycyclopentadiene dialdehydes can then be condensed with phenols to form polycyclopentadiene polyphenols. Polycyclopentadiene can be prepared by heating cyclopentadiene to temperatures above 100°

C. as discussed in Kirk-Othmer, ENCYCLOPEDIA OF CHEMICAL TECHNOLOGY, Fifth Edition, Vol. 8, p. 223 (2010). All of the aforementioned references are incorporated herein in their entirety by reference.

The hydroformylation can occur at a pressure of 1 to 250 atmospheres and a temperature of 20° C. to 250° C. The syngas can include varying amounts of carbon monoxide and hydrogen. The syngas can include one or more inert gases, such as nitrogen.

The hydroformylation can be conducted using a rhodium catalyst without a ligand and at a syngas pressure of 200 to 350 atmospheres as discussed in U.S. Pat. No. 7,321,068. Examples of suitable ligands include, but are not limited to, carbon monoxide and organophosphine ligands having the general formula $PR^1R^2R^3$ where each $R^1$, $R^2$, and $R^3$ is a substituted or unsubstituted alkyl group, an aryl, an aralkyl, an alkaryl, a halide, or a combination thereof. A specific example includes, but is not limited to, n-butyldiphenylphosphine. An example of a suitable catalyst includes, but is not limited to, $Rh(CO)_2$(acetylacetonate).

During the hydroformylation amounts, such as 5 to 25 weight (wt.) percent (%) or less of the total reaction products, of polycyclopentadiene monoaldehydes, having varying degrees of saturation, may also be produced along with the polycyclopentadiene dialdehydes. An example of these polycyclopentadiene monoaldehydes is represented by the following Formula III, where n is as described herein:

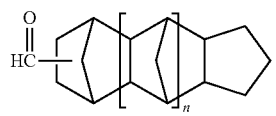

Formula III

The polycyclopentadiene monoaldehydes can be separated from the polycyclopentadiene dialdehydes. For example, a distillation process can be used to separate the polycyclopentadiene monoaldehydes from the polycyclopentadiene dialdehydes. However, using a mixture of the polycyclopentadiene monoaldehydes and the polycyclopentadiene dialdehydes can help control a level of functionality. For example, whereas novolac chemistry can be used to form the polycyclopentadiene polyphenols from the polycyclopentadiene dialdehydes, novolac chemistry can also be used to form polycyclopentadiene diphenols from the polycyclopentadiene monoaldehydes. An example of the polycyclopentadiene diphenols having a saturated cyclopentane ring is represented by the following Formula IV:

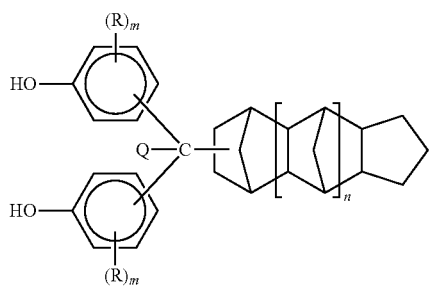

Formula IV where n, m, R and Q are as described herein. Oligomers may also be present in the polycyclopentadiene diphenols. Thus, mixtures of polycyclopentadiene diphenols and polycyclopentadiene polyphenols may be produced.

The hydroformylation can produce isomeric ketones as described by Longoni. These ketones can be the predominant products when the hydrogen/carbon monoxide pressure is low (~1 atm). If these ketones are present in the product mix they can be condensed with phenol to form polyphenols of Formula V, where n, m, and R are as described herein.

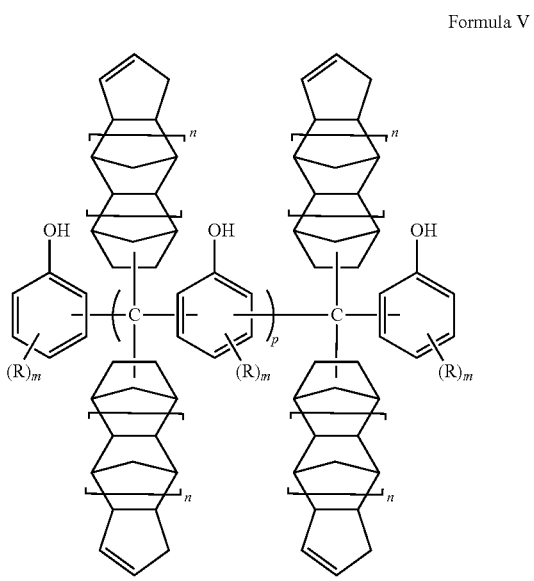

Formula V

Using mixtures of the polycyclopentadiene monoaldehydes, polycyclopentadiene dialdehydes, and ketones may help control the level of functionality in a given thermosettable composition. For example, crosslink density for a thermosettable composition of the present disclosure can be adjusted (e.g., decreased or increased) based on the relative amounts of the polycyclopentadiene polyphenols and the polycyclopentadiene diphenols used in preparing the vinylbenzyl ethers of polycyclopentadiene polyphenol. Adjusting the level of functionality in this way can allow for the properties, such as glass transition temperature (Tg), of the products obtained by curing the thermosettable compositions to be tailored to desired levels and/or balance with other properties, such as toughness, of the product.

Moreover, it may be possible to control the amount of dicyclopentadiene and/or polycyclopentadiene moieties in the polycyclopentadiene dialdehydes. The dicyclopentadiene and/or polycyclopentadiene can be formed through Diels-Alder chemistry using cyclopentadiene where, as discussed herein, the average value for n can be from zero to 20. So, for example, when the polycyclopentadiene moities in the polycyclopentadiene dialdehydes are oligomers they can have a distribution of n values that is on average from 2 to 5. For other applications, n can have a value of zero or 1. The ability to control the dicyclopentadiene and/or polycyclopentadiene moities in the polycyclopentadiene dialdehydes may also allow for the ability to control and/or tailor a crosslink density of a thermosettable composition while retaining some properties of the cured product.

The resulting polycyclopentadiene dialdehydes along with any of the polycyclopentadiene monoaldehydes and ketones can then undergo a novolac reaction to form polycyclopentadiene polyphenols. The novolac reaction involves the use of a phenol and an acid catalyst. For example, the polycyclopentadiene dialdehydes and molten phenol can be reacted at a temperature of 65° C. to 70° C. with stirring under a nitrogen atmosphere and in the presence of an acid catalyst. The resulting polycyclopentadiene dialdehydes, along with any of the polycyclopentadiene monoaldehydes, can then undergo a novolac reaction to form polycyclopentadiene polyphenols.

Polycyclopentadiene polyphenols can be prepared via a condensation reaction of a mole ratio of the polycyclopentadiene dialdehydes (and any polycyclopentadiene monoaldehydes) to phenol and/or substituted phenol, o-cresol, m-cresol, p-cresol, 2,4-dimethylphenol, 2,6-dimethylphenol, 1-naphthol, and 2-naphthol of 1:20 to 1:6, and preferably from 1:15 to 1:8; in the presence of an acid catalyst which is preferably from 0.1 to 2 wt. %, and more preferably from 0.1 to 1 wt. % based on the amount of phenol or substituted phenol compound employed. Higher mole ratios than 1:20 of the phenol or substituted phenol may be employed, however doing may require additional energy and thus expense to recover and recycle the excess phenol and/or substituted phenol.

Condensation reactions employing a large excess of the phenol and/or substituted phenol have been found to favor polycyclopentadiene polyphenols having a low polydispersity and weight average molecular weight. Likewise, as the amount of the phenol and/or substituted phenol is reduced, there can be an increase in oligomers of the polycyclopentadiene polyphenols, increasing the weight average molecular weight. Increased oligomer content favors higher hydroxyl functionality per molecule which may be highly beneficial for certain end uses but at the cost of higher viscosity. For some applications, very large excesses of phenol and/or substituted phenol may be employed; the molar ratio provided above can produce products rich in polycyclopentadiene polyphenol, and low in oligomers.

ric acid; metal oxides, such as zinc oxide, aluminum oxide, magnesium oxide; organic acids, such as p-toluenesulfonic acid, oxalic acid, 3-mercapto-1-propane sulfonic acid, and combinations thereof. 3-mercapto-1-propane sulfonic acid is a preferred acid catalyst or co-catalyst as it is highly selective in forming the polycyclopentadiene polyphenols and can eliminate a need for an azeotropic removal of water from the reaction products. The water can remain in the reactor, without quenching the novolac reaction.

Reaction temperatures and times vary, but can be from 5 minutes to 48 hours and reaction temperatures of from 20° C. to 175° C. may be employed. Preferably reaction temperatures and times can be from 15 minutes to 36 hours and reaction temperatures of from 30° C. to 125° C. Most preferably reaction temperatures and times can be from 30 minutes to 24 hours and reaction temperatures of from 35° C. to 75° C.

At the end of the reaction, the acidic catalyst can be removed by neutralization, for example by washing or extracting with water. Likewise, at the end of the reaction, excess phenol can be removed from the novolac product, for example, by distillation or extraction.

The polycyclopentadiene polyphenols can have a polydispersity index of less than 2. For example, the polydispersity index (the measure of distribution of molecular mass in a given polymer sample) of the polycyclopentadiene polyphenols can be from 1.3 to 1.4. These types of results indicate that both the n values and the p values of the polycyclopentadiene polyphenols are very uniform. Having a uniform chain length for the polycyclopentadiene polyphenols can allow for more desirable viscosity predictability in the viscosity of the thermosettable compositions of the present disclosure.

The polycyclopentadiene polyphenols can be represented by the following Formula VI:

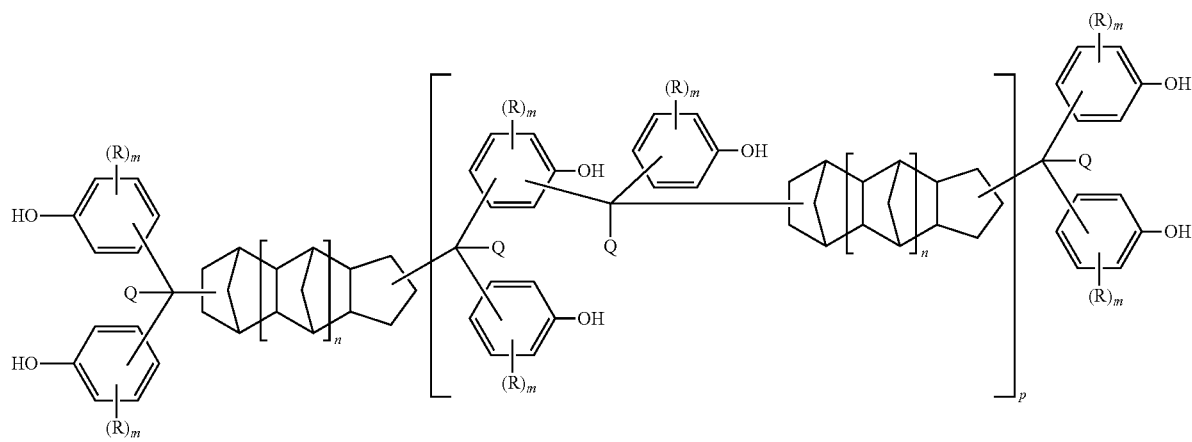

Formula VI

A solvent can be employed when forming the polycyclopentadiene polyphenols. With some phenols having relatively higher melt viscosities than some other phenols use of one or more solvents may be beneficial for maintaining a suitable reaction medium. The solvent can be inert to the reaction and/of the reaction products. The solvent may serve as an agent for the azeotropic removal of water from the condensation reaction. Examples of the solvent include, but are not limited to, toluene and xylene.

Suitable acid catalysts include, but are not limited to, protonic acids, such as hydrochloric acid, sulfuric acid, phosphowhere n, m, p, R and Q are as described herein. For the polycyclopentadiene polyphenols, when m has a value other than zero, the carbon bonded to Q

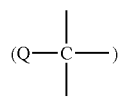

is preferably in the ortho and/or para position relative to the —OX group. It is appreciated that mixtures of compounds having the carbon bonded to the Q in both the ortho and the para position relative to the —OX group are possible. It is also possible to have the carbon bonded to Q

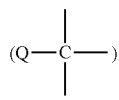

in the meta position relative to the —OX group. Polycyclopentadiene polyphenols are discussed in U.S. Utility Application Ser. No. 61/329320, titled "POLYCYCLOPENTADIENE COMPOUNDS", The Dow Chemical Company filed herewith, the disclosure which is incorporated herein by reference.

As discussed herein, the disclosed vinylbenzyl ethers of polycyclopentadiene polyphenol can be obtained by reacting polycyclopentadiene polyphenol, with a stoichiometric excess of a vinylbenzyl halide per phenolic hydroxyl group in the presence of a stoichiometric excess of a base compound per phenolic hydroxyl group and in the presence of a solvent.

Examples of the vinylbenzyl halide include, but are not limited to, o-vinylbenzyl chloride, m-vinylbenzyl chloride, p-vinylbenzyl chloride, o-vinylbenzyl bromide, m-vinylbenzyl bromide, p-vinylbenzyl bromide, and 3-vinyl-5-methyl benzyl chloride. For some applications a combination of vinylbenzyl halides can be employed. Various ratios of vinylbenzyl halide to phenolic hydroxyl group, wherein the vinylbenzyl halide is in stoichiometric excess, are possible.

The base compound can be an inorganic base. Examples of inorganic bases include, but are not limited to, lithium hydroxide, sodium hydroxide, potassium hydroxide. The base compound can be a tertiary amine. Examples of tertiary amines include, but are not limited to, trimethylamine and triethylamine. For some applications a combination of base compounds can be employed. For some applications lithium hydroxide is the most preferred base compound. Various ratios of base compound to phenolic hydroxyl group, wherein the base compound is in stoichiometric excess, are possible.

Examples of the solvent include, but are not limited to, water, alcohols, aliphatic ketones, chlorinated hydrocarbons, aliphatic ethers, cycloaliphatic ethers, aliphatic diethers, cycloaliphatic diethers, and aromatic hydrocarbons. For some applications the most preferred solvent is selected from the group consisting of water, methanol, acetone, and combinations thereof. An effective amount of the solvent can be employed so as to maintain reactants in solution for reaction, to suspend, the reaction products, and/or to prevent excessive viscosity in the reaction which can hinder mixing and heat transfer, and for other reasons which will readily be apparent to the skilled artisan. The effective amount of the solvent may vary as a function of the specific combination of reactants and solvent(s) employed for a particular application. The effective amount of the solvent can be from about 25 to 250% by wt. with respect to a weight of the polycyclopentadiene polyphenol reactant employed. Additional amounts of one or more solvents can be employed for processing of the product, specifically for isolation and purification of said product.

For some applications the base compound and the solvent can be combined before being employed in the polycyclopentadiene polyphenol and vinylbenzyl halide reaction. For example, a methanolic potassium hydroxide solution can be formed from methanol and potassium hydroxide and the methanolic potassium hydroxide solution can then be employed when reacting the polycyclopentadiene polyphenol with the vinylbenzyl halide.

When reacting the polycyclopentadiene polyphenol with the vinylbenzyl halide to obtain the vinylbenzyl ethers of polycyclopentadiene polyphenol a polymerization inhibitor may be employed. A polymerization inhibitor may also be beneficially added to the final product. Examples of the polymerization inhibitor include, but are not limited to, hindered phenols, such as 2,6-di-tertiary-butyl-4-methylphenol and 4-tertiary-butylcatechol; nitrophenols, such as 4,6-dinitro-o-cresol; nitroalkanes, such as nitromethane; and benzoquinone, hydroquinone, phenothiazine, 2,2,6,6-tetramethylpiperidine, 1-oxyl; mixtures thereof and the like. The amount of the polymerization inhibitor employed can depend upon the structure of the individual polymerization inhibitor or mixture of polymerization inhibitors used, the desired shelf life for the product, the atmosphere surrounding the product, the stage at which the polymerization inhibitor is anticipated to be added, for example, as a process inhibitor or as an inhibitor for the final isolated product, and other such reasons that will be apparent to the skilled artisan. An effective, amount of the polymerization inhibitor can be employed. The effective amount can be from 10 parts per million to 0.5% by weight.

The reaction of the polycyclopentadiene polyphenol, with the vinylbenzyl halide can occur at a temperature of 10° C. to 100° C. For some applications a reaction temperature of 20° C. to 75° C. is preferred, and for some applications a reaction temperature of 25° C. to 60° C. is most preferred. For one or more embodiments, the reaction time can be from 2 hours to 7 days. For some applications a reaction time from 2 hours to 24 hours is preferred.

The disclosed vinylbenzyl ethers of polycyclopentadiene polyphenol can be included in a thermosettable composition. The thermosettable composition can be a solid phase, such as a powder, or a liquid phase, such as a solution, that includes the vinylbenzyl ethers of polycyclopentadiene polyphenol. The vinylbenzyl ethers of polycyclopentadiene polyphenol can have various n values and various p values, as described herein. For such mixtures the values of n and p can be described as number values for the average extent of oligomerization.

For one or more embodiments, the thermosettable composition is cured to form a product that is a homopolymer. A homopolymer is a polymer derived from one species of monomer. Herein the disclosed vinylbenzyl ethers of polycyclopentadiene polyphenol are considered to be one species of monomer.

For one or more embodiments, the thermosettable composition is cured to form a product that is a copolymer. A copolymer is a polymer derived from two or more species of monomers. The two or more species of monomers can be referred to as comonomers. Herein one of the two or more species of monomers that is one of the comonomers is the disclosed vinylbenzyl ether of polycyclopentadiene polyphenol. For one or more embodiments a comonomer is selected from the group consisting of polymaleimides, polycyanates, polycyanamides, epoxy compounds, compounds containing one or more polymerizable ethylenically unsaturated group(s), and combinations thereof. For the various embodiments the thermosettable compositions including comonomers have a minimal active level of the vinylbenzyl ethers of polycyclopentadiene polyphenol. This minimal active level can have different values depending upon the particular application. For example, an application where a lower cure enthalpy is desirable may have a different minimal active level of the vinylbenzyl ethers of polycyclopentadiene polyphenol that another application where an increased glass transition temperature is desirable. For one or more embodiments the comonomer selected from the group consisting polymaleimides, polycyanates, polycyanamides, epoxy compounds, compounds containing one or more polymerizable ethylenically unsaturated group(s), and combinations thereof can be 5 weight percent to 90 weight percent of the monomers included in the thermosettable composition from which the copolymer is derived. Thus, for one or more embodiments the vinylbenzyl ethers of polycyclopentadiene polyphenol are 10 weight percent to 95 weight percent of the monomers from which the copolymer is derived.

Herein, polymaleimides are compounds having two or more maleimide moieties. Examples of polymaleimides include, but are not limited to, 1,2-bismaleimido ethane; 1,4-bismaleimido butane; 1,6-bismaleimido hexane; 1,12-bismaleimido dodecane; 1,6-bismaleimido-(2,2,4-trimethyl) hexane; 1,3-bismaleimido benzene; 1,4-bismaleimido benzene; 4,4'-bismaleimido diphenyl methane; 4,4'-bismaleimido diphenyl ether; 4,4'-bismaleimido diphenyl sulfide; 4,4'-bismaleimido diphenyl sulfone; 4,4'-bismaleimido dicyclohexyl methane; 2,4-bismaleimido toluene; and 2,6-bismaleimido toluene.

Herein, polycyanates are compounds having two or more cyanate moieties. Examples of polycyanates include, but are not limited to, bisphenol A dicyanate, hexafluorobisphenol A dicyanate, tetramethylbisphenol F dicyanate, polycyanate of dicyclopentadiene polyphenol; 2-tert-butyl-1,4-dicyanatobenzene; 2,4,6-trimethyl-1,3-dicyanatobenzene; 4-chloro-1, 3-dicyanatobenzene; 1,3,5-tricyanatobenzene; 4,4'-dicyanatodiphenyl; 2,2'-dicyanato-1,1'-binaphthyl; 4,4'-dicyanatodiphenyl ether; 3,3', 5,5'-tetramethyl-4,4'-dicyanatodiphenyl ether; 3,3',5,5'-tetrachloro-4,4'-dicyanatodiphenyl ether; 4,4'-bis-[p-cyanatophenoxy] diphenyl ether; 4,4'-bis-[p-cyanatophenyl isopropyl] diphenyl ether; 4,4'-bis-[p-cyanatophenoxy]benzene; 4,4'-bis-[m-cyanatophenoxy]diphenyl ether; 4,4'-bis-[4-(4-cyanatophenoxy)-phenyl sulphone]diphenyl ether; 4,4'-dicyanatodiphenyl sulphone; 3,3', 5,5'-tetramethyl-4,4'-dicyanato diphenyl sulphone; 3,3',5,5'-tetrachloro-4,4'-dicyanatodiphenyl sulphone; 4,4'-bis-[p-cyanatophenyl isopropyl]diphenyl sulphone; 4,4'-bis-[(4-cyanato)phenoxy]-diphenyl sulphone; 4,4'-bis-[(3-cyanato)phenoxy] diphenyl sulphone; 4,4'-bis-[4-(4-cyanatophenyl isopropyl) phenoxy]-diphenyl sulphone; 4,4'-bis-[4-(4-cyanatophenyl sulphone)phenoxy]diphenyl sulphone; and 4,4'-bis-[4-(4-cyanato)diphenoxy]diphenyl sulphone.

Herein, polycyanamides are compounds having two or more cyanamide moieties. Examples of polycyanamides include, but are not limited to, the dicyanamides of 4,4'-diminodiphenylmethane; 4,4'-sulfonyldianiline; 4,4'-diaminodiphenyl oxide; 3,3'-dimethyl-4,4'-diaminobiphenyl; 4,4'-diaminostilbene; 4,4'-diaminophenyl benzoate; 4,4'-diamino-alpha-methylstilbene; tris(aminophenyl)methane; aniline-formaldehyde condensation products; the cyanamides of 4-amino-4'-hydroxybenzanilide; 4-amino-4'-hydroxystilbene; and p-aminophenol.

An epoxy compound is a compound in which an oxygen atom is directly attached to two adjacent or non-adjacent carbon atoms of a carbon chain or ring system to form an epoxide or oxirane ring. The epoxy compound can be selected from the group consisting of aromatic epoxy compounds, alicyclic epoxy compounds, aliphatic epoxy compounds, and combinations thereof.

Examples of aromatic epoxy compounds include, but are not limited to, glycidyl ether compounds of polyphenols, such as hydroquinone, resorcinol, bisphenol A, bisphenol F, 4,4'-dihydroxybiphenyl, phenol novolac, cresol novolac, trisphenol (tris-(4-hydroxyphenyl)methane), 1,1,2,2-tetra(4-hydroxyphenyl)ethane, tetrabromobisphenol A, 2,2-bis(4-hydroxyphenyl)-1,1,1,3,3,3-hexafluoropropane, and 1,6-dihydroxynaphthalene.

Examples of alicyclic epoxy compounds include, but are not limited to, polyglycidyl ethers of polyols having at least one alicyclic ring, or compounds including cyclohexene oxide or cyclopentene oxide obtained by epoxidizing compounds including a cyclohexene ring or cyclopentene ring with an oxidizer. Some particular examples include, but are not limited to, hydrogenated bisphenol A diglycidyl ether; 3,4-epoxycyclohexylmethyl-3,4-epoxycyclohexyl carboxylate; 3,4-epoxy-1-methylcyclohexyl-3,4-epoxy-1-methylhexane carboxylate; 6-methyl-3,4-epoxycyclohexylmethyl-6-methyl-3,4-epoxycyclohexane carboxylate; 3,4-epoxy-3-methylcyclohexylmethyl-3,4-epoxy-3-methylcyclohexane carboxylate; 3,4-epoxy-5-methylcyclohexylmethyl-3,4-epoxy-5-methylcyclohexane carboxylate; bis(3,4-epoxycyclohexylmethyl)adipate; methylene-bis(3,4-epoxycyclohexane); 2,2-bis(3,4-epoxycyclohexyl)propane; dicyclopentadiene diepoxide; ethylene-bis(3,4-epoxycyclohexane carboxylate); dioctyl epoxyhexahydrophthalate; and di-2-ethylhexyl epoxyhexahydrophthalate.

Examples of aliphatic epoxy compounds include, but are not limited to, polyglycidyl ethers of aliphatic polyols or alkylene-oxide adducts thereof, polyglycidyl esters of aliphatic long-chain polybasic acids, homopolymers synthesized by vinyl-polymerizing glycidyl acrylate or glycidyl methacrylate, and copolymers synthesized by vinyl-polymerizing glycidyl acrylate or glycidyl methacrylate and other vinyl monomers. Some particular examples include, but are not limited to glycidyl ethers of polyols, such as 1,4-butanediol diglycidyl ether; 1,6-hexanediol diglycidyl ether; a triglycidyl ether of glycerin; a triglycidyl ether of trimethylol propane; a tetraglycidyl ether of sorbitol; a hexaglycidyl ether of dipentaerythritol; a diglycidyl ether of polyethylene glycol; and a diglycidyl ether of polypropylene glycol; polyglycidyl ethers of polyether polyols obtained by adding one type, or two or more types, of alkylene oxide to aliphatic polyols such as propylene glycol, trimethylol propane, and glycerin; and diglycidyl esters of aliphatic long-chain dibasic acids.

A compound containing one or more polymerizable ethylenically unsaturated group(s) can be a monoethylenically unsaturated monomer or a polyethylenically unsaturated monomer. Examples of compounds containing one or more polymerizable ethylenically unsaturated group(s) include, but are not limited to, those described in U.S. Pat. No. 5,428, 125, which is incorporated herein in its entirety by reference.

Additionally, as is known in the art, it is possible to add other thermosetting monomers such as non-glycidyl ether di or polyepoxides, di or polyisocyanates, and benzoxazines, as well as other oligomers or polymers such as poly(phenylene oxide) to the disclosed thermosettable compositions.

For one or more embodiments the thermosettable composition includes a solvent. Examples of solvents include, but are not limited to, ketones, amides, alcohols, and esters. Examples of ketones include, but are not limited to, acetone, methyl ethyl ketone, and cyclohexanone. Examples of amides include, but are not limited to, N,N-dimethylformamide, N,N-dimethylacetamide, and N-methylpyrrolidinone. Examples of alcohols include, but are not limited to, methanol, ethanol, isopropanol, and Dowanol™ PM. Examples of esters include, but are not limited to, methyl acetate, ethyl acetate, and Dowanol™ PMA. The solvent can be 10 weight percent to 75 weight percent of a total weight of the thermosettable composition, where the total weight is based upon the monomers and solvent comprising the thermosettable composition.

For one or more embodiments the thermosettable composition includes an additive. Examples of additives include, but are not limited to, polymerization catalysts, co-curing agents, flame retardants, synergists for flame retardants, solvents, fillers, adhesion promoters, wetting aids, dispersing aids, surface modifiers, thermoplastic resins, mold release agents, and combinations thereof Examples of polymerization catalysts include, but are not limited to, transition metal complexes, imidazoles, phosphonium salts, phosphonium complexes, tertiary amines, hydrazides, "latent catalysts" such as Ancamine® 2441 and K61B (modified aliphatic amines available from Air Products and Chemicals, Inc.), Ajinomoto Fine-Techno Co., Inc. Ajicure PN-23 or MY-24, modified ureas, and combinations thereof.

Examples of co-curing agents include, but are not limited to, dicyandiamide, substituted guanidines, phenolics, amino compounds, benzoxazine, anhydrides, amidoamines, polyamides, and combinations thereof.

Examples of flame retardants and/or synergists for flame retardants include, but are not limited to, phosphorus containing molecules such as H-DOP (9,10-dihydro-9-oxa-10-phosphaphenanthrene-10-oxide) reaction products, magnesium hydrate, zinc borate, metallocenes, and combinations thereof.

Examples of fillers include, but are not limited to, silica, alumina trihydrate, aluminum oxide, metal oxides, carbon nanotubes, silver flake or powder, carbon black, graphite, and combinations thereof. The filler can be functional and/or non-functional. For various applications, the filler can have a particle size range of from 0.5 nm to 100 μm.

Examples of adhesion promoters include, but are not limited to, modified organosilanes (epoxidized, methacryl, amino, allyl, etc.), acetylacetonates, sulfur containing molecules, titanates, zirconates, and combinations thereof.

Examples of wetting aids and/or dispersing aids include, but are not limited to, modified organosilanes such as, e.g., BYK®-W 900 series and W 9000 series (BYK Additives & Instruments), and modified fluorocarbons.

Examples of surface modifiers include, but are not limited to, slip additives and gloss additives, such as those available from BYK Additives & Instruments.

Examples of thermoplastic resins include, but are not limited to, polyphenylsulfones, polysulfones, polyethersulfones, polyvinylidene fluoride, polyetherimides, polyphthalimides, polybenzimidazoles, acrylics, phenoxy resins, polyurethanes, and combinations thereof The thermoplastic resin can be reactive and/or non-reactive.

Examples of mold release agents include, but are not limited to, waxes such as, e.g., carnauba wax.

For one or more embodiments, the products that are formed by curing the disclosed thermosettable compositions are crosslinked polymers, which can be said to be thermoset. These products can include an infusible polymer network that can soften when heated, but will not melt or flow.

For one or more embodiments, the present disclosure provides a B-staged product that is obtainable by curing the thermosettable composition. The B-staged product can be formed by a process that includes contacting a reinforcement component and a matrix component. The matrix component surrounds and/or supports the reinforcement component. The matrix component and the reinforcement component provide a synergism. This synergism provides that products obtained by curing the B-staged products have mechanical and/or physical properties that are unattainable with only the individual components. The thermosettable compositions, as disclosed herein, are useful as the matrix component.

The reinforcement component can be a fiber. Examples of fibers include, but are not limited to, glass, aramid, carbon, polyester, polyethylene, quartz, metal, ceramic, biomass, and combinations thereof. The fibers can be coated. An example of a fiber coating includes, but is not limited to, boron.

Examples of glass fibers include, but are not limited to, A-glass fibers, E-glass fibers, C-glass fibers, R-glass fibers, S-glass fibers, and T-glass fibers. Aramids are organic polymers, examples of which include, but are not limited to, Kevlar® and Twaron®. Examples of carbon fibers include, but are not limited to, those fibers formed from polyacrylonitrile, pitch, rayon, and cellulose. Examples of metal fibers include, but are not limited to, stainless steel, chromium, nickel, platinum, titanium, copper, aluminum, beryllium, and tungsten. Examples of ceramic fibers include, but are not limited to, those fibers formed from aluminum oxide, silicon dioxide, zirconium dioxide, silicon nitride, silicon carbide, boron carbide, boron nitride, and silicon boride. Examples of biomass fibers include, but are not limited to, those fibers formed from wood and non-wood.

The reinforcement component can be a fabric. The fabric can be formed from the fiber as discussed herein. Examples of fabrics include, but are not limited to, stitched fabrics and woven fabrics. The fabric can be unidirectional or multiaxial. The reinforcement component can be a combination of the fiber and the fabric.

For the B-staged product, the reinforcement component can be exposed to the matrix component via rolling, dipping, spraying, or some other procedure. After the reinforcement component has been exposed to the matrix component a portion of the solvent that is present in the thermosettable composition can be removed via volatilization by heating. The heating can be at a temperature of 90° C. to 200° C., however for some applications the heating can occur at another temperature. While and/or after solvent is removed the matrix component can be partially cured. This partial curing can be referred to as B-staging. The B-staged product can be referred to as a prepreg. B-staging can occur at a temperature of 90° C. to 200° C.; however for some applications the B-staging can occur at another temperature.

The B-staged products can be layered or formed into a shape. For some applications where an electrical laminate is being produced, layers of the B-staged product can be alternated with layers of a conductive material. An example of the conductive material includes, but is not limited to, copper foil. The B-staged product layers can then be exposed to conditions so that the matrix component becomes more fully cured. For example, the B-staged product layers can be exposed to a temperature of 90° C. to 230° C. for a period of time of 10 minutes to 500 minutes. Additionally the B-staged product can be exposed to a pressure of 50 N/cm$^2$ to 500 N/cm$^2$. In this curing process the matrix component on the reinforcement component can flow and mix with the matrix component on adjacent layers thereby fusing the layers together.

The disclosed thermosettable compositions and/or the disclosed B-staged products can be cured to provide products that include, but are not limited to, protective coatings, electrical laminates, structural laminates, composite materials, filament windings, moldings, castings, encapsulations, packagings, and adhesives, among others. Properties of these products can include desirable glass transition temperatures, solvent resistance, moisture resistance, abrasion resistance, and toughness.

EXAMPLES

Materials

Rh(CO)$_2$(acetylacetonate) available from Strem Chemicals Inc.

n-butyldiphenylphosphine available from Organometallics, Inc (E. Hampstead, N.H., USA).

Dicyclopentadiene available from The Dow Chemical Company.

Syngas (1:1 molar ratio CO:H$_2$) available from Airgas Great Lakes, Inc.

KBr plate available from Sigma-Aldrich.

KBr pellet available from Sigma-Aldrich.

3-Mercaptopropane-1-sulfonic acid, sodium salt (90% purity) available from Sigma-Aldrich.

Hydrochloric acid, A.C.S. reagent grade, 37.5% by acid base titration, available from Mallinckrodt Baker, Inc.

Phenol, >99%, available from The Dow Chemical Company.

Anhydrous acetone available from Sigma-Aldrich.

Cyanogen bromide available from Sigma-Aldrich.

Triethylamine available from Sigma Aldrich.

Dichloromethane, 99.8%, available from Sigma Aldrich.

Anhydrous sodium sulfate available from Sigma-Aldrich.

Bisphenol A dicyanate available from available from Huntsman International LLC as AroCy B-10 Monomeric Bisphenol A Dicyanate.

Anhydrous methanol available from Sigma-Aldrich.

Lithium hydroxide available from Sigma-Aldrich.

Vinylbenzyl chloride (43% para/57% meta isomer mixture) available from Sigma-Aldrich.

Diatomaceous earth available as Celite® 545, from Celite Corporation.

Preparation of Dicyclopentadiene Dialdehyde

Rh(CO)$_2$(acetylacetonate) (35.1 mg; 0.136 mmol), n-butyldiphenylphosphine (0.33 g; 1.36 mmol), and dicyclopentadiene (70 g) were combined in a nitrogen atmosphere purge box to form a solution. The solution was placed in a 150 mL Parr reactor and sparged three times with syngas at 20° C. Then, the solution was heated to 100° C. at a syngas pressure of 90 psi while being stirred to form 97.7 g of a brown liquid. The reaction was monitored using an Agilent 6890 Gas Chromatography system. Gas Chromatography (GC) analysis of the brown liquid showed dicyclopentadiene dialdehyde (87 area % in GC at 10.4-10.7 min) and dicyclopentadiene monoaldehyde (6 area % in GC at 5.6 and 6.0 min). Gas chromatographic/mass spectroscopic (GC/MS) analysis of the brown liquid with the Agilent 6890 and a Agilent 5973 Mass Spectrometer indicated the formation of the desired dicyclopentadiene dialdehyde (M$^+$=192) and saturated dicyclopentadiene monoaldehyde (M$^+$=164). $^1$H NMR ($\delta$, CDCl$_3$, ppm): 1.2-2.8 m (17H, CH+CH$_2$), 9.28-9.57 m (2H, CHO). $^{13}$C NMR ($\delta$, CDCl$_3$, ppm): 23.66; 23.81; 24.35; 25.90; 25.97; 27.82; 27.97; 29.45; 29.63; 40.65; 40.92; 41.03; 41.38; 45.42; 45.50; 45.58; 45.64; 45.70; 46.07; 46.11; 48.36; 48.65; 49.17; 53.17; 53.21; 54.57; 202.86; 202.89; 202.92; 202.95; 203.03; 203.07; 203.09; 203.14

Fourier transform infrared spectrophotometric (FTIR) analysis of a neat film of the brown liquid on a KBr plate via a Nicolet Avatar 3700 DTGS FTIR (Thermo Electron Corporation) showed a strong aldehyde carbonyl stretch at 1720.4 cm$^{-1}$.

Preparation of 3-mercapto-1-propane sulfonic acid catalyst

3-Mercaptopropane-1-sulfonic acid, sodium salt was added to concentrated hydrochloric acid (35.7% aqueous, 200 mL) which was magnetically stirred in a glass beaker. After covering with a sheet of Parafilm "M" (American National Can, Greenwich, Conn.) to prevent uptake of atmospheric moisture, the resulting white crystalline slurry was stirred for 5 minutes then filtered over a medium fitted glass funnel. The filtrate was rotary evaporated to give 8.88 g of a pale yellow tacky solid product which was used as the catalyst without further processing.

Phenolation Reaction

Dicyclopentadiene dialdehyde, as prepared above, (48.06 grams, 0.25 mole uncorrected) and molten phenol (470.5 grams, 5.0 moles) were added to a 1 liter glass three neck round bottom reactor. The reactor included an ambient temperature (22° C.) condenser, a thermometer, both affixed to the reactor via a Claisen adaptor, and an overhead nitrogen inlet, a glass stirring shaft with a Teflon™ stirrer blade coupled to a variable speed motor, and a thermostatically controlled heating mantle. Overhead nitrogen flow (0.5 liter per min) was established and the contents of the reactor were heated to 65° C. over twenty minutes while being stirred to provide a transparent yellow colored solution. Catalyst, as prepared above, (0.39 g) was added to the contents of the reactor resulting in a peak exotherm of 70° C. after 3 minutes and a dark amber solution. The heating mantle was removed from the reactor, and a fan was used to cool the reactor exterior to 65° C. Further catalyst (0.22 g) was added to the contents of the reactor resulting in a peak exotherm of 66° C. after one minute; again the reactor exterior was cooled to 65° C. Further catalyst (0.35 g) was added to the contents of the reactor resulting in a peak exotherm of 68° C. after 2 minutes; again the reactor exterior was cooled to 65° C. Further catalyst (0.24 g) was added to the contents of the reactor and the reactor exterior maintained a temperature of 65° C. After 5 minutes further catalyst (0.37 g) was added to the contents of the reactor and the reactor exterior decreased from 65° C. to 62.5° C. over 5 minutes. The fan was removed and the heating mantle was returned to the reactor. Further catalyst (0.38 g) was added to the contents of the reactor and the reactor exterior was maintained at 65° C. for 22.25 hours while high pressure liquid chromatographic (HPLC) analysis was used to monitor the contents of the reactor. The HPLC included a Hewlett Packard 1090 Liquid Chromatograph using a Zorbax Eclipse® (Agilent) XDB-C8 analytical column (5µ, 4.6×150 mm) with an Eclipse® (Agilent) XDB-C8 analytical guard column (5µ, 4.6×12.5 mm). The columns were maintained in a chromatograph oven at 40° C. Acetonitrile and water (treated with 0.05% aqueous o-phosphoric acid) were used as the eluents and were initially delivered via pump at a rate of 1.000 mL per minute as a 70/30% solution, respectively, changing after 5 minutes to a 90/10% solution and held therein for the next 15 minutes. The acetonitrile used,was HPLC grade, 100.0% purity (by gas chromatography), with a UV cutoff of 189 nm. The o-phosphoric acid used was nominally 85% pure (actual assay 85.1%). The water used was HPLC grade. A diode array detector employed for the sample analysis was set at 225 nm and the reference was set at 550 nm. The total catalyst used was 1.95 grams, which was 0.05 mole % with respect to the dicyclopentadiene dialdehyde. At 1.6 hours after the final catalyst addition, HPLC analysis indicated full conversion of the dicyclopentadiene dialdehyde to a distribution of products.

After the 22.25 hours the contents of the reactor were equally divided into a pair of beakers that each contained 3 liters of deionized (DI) water. The contents of each beaker were stirred for 75 minutes; then, the contents of each beaker settled for approximately 12 hours. After settling each beaker was decanted to a volume of 500 milliliters and the decanted aqueous portion was discarded. Additional DI water was added to each beaker so that each beaker had a 3.5 liter total volume; each beaker's contents was stirred and heated to 50° C. Viscous strings of reddish amber colored compound formed in the bottom of each beaker. The contents of each beaker again settled for approximately 12 hours and after settling each beaker was decanted and the decanted aqueous portion was discarded. Boiling DI water (1.5 liters) was added to the dark yellow orange colored product remaining in each beaker while the contents of each beaker was stirred and heated to boil. After boiling the contents of each beaker were allowed to cool to 22° C. while being stirred; after which solids from each beaker were collected via decanting through filter paper. The collected solids were placed in a ceramic dish and then into a vacuum oven heated to 100° C. for 16 hours. Then the solids were ground to a fine powder and returned to the vacuum oven for an additional 6.5 hours to yield 119.79 grams of dicyclopentadiene polyphenol, which was observed to be a mustard yellow colored powder. FTIR analysis of the dicyclopentadiene polyphenol indicated complete disappearance of the aldehyde carbonyl stretch at 1720.4 $cm^{-1}$ and a strong aromatic ring absorbance at 1610.9 $cm^{-1}$ (shoulder at 1595.7) and 1510.0 $cm^{-1}$, a broad strong hydroxyl O—H stretching centered at 3382.2 $cm^{-1}$, and a broad strong C—O stretching at 1226.7 $cm^{-1}$ (shoulder at 1170.7). HPLC analysis indicated 12 components with 6 predominant components comprising 27.9, 4.2, 6.8, 11.0, 21.6 and 22.2 area % respectively.

Comonomer Synthesis (Dicyclopentadiene Polycyanate)

Dicyclopentadiene polyphenol, as prepared above, (26.63 grams, nominally 0.02 hydroxyl equivalent) and anhydrous acetone (250 milliliters) were added to a 500 milliliter, three neck, round bottom glass reactor that was equipped with a condenser (maintained at 0° C.), a thermometer, an overhead nitrogen inlet (1 liter per minute $N_2$ used), and magnetic stirrer. Cyanogen bromide (22.67 grams, 0.0214 mole, 1.07:1 cyanogen bromide:hydroxyl equivalent ratio) was added to the contents of the reactor while stirring. A dry ice-acetone bath was placed under the reactor and the stirred contents of the reactor were cooled to −6° C. Triethylamine (20.64 grams, 0.0204 mole, 1.02 triethylamine:hydroxyl equivalent ratio) was added to the contents of the reactor, which were maintained at a temperature of −8° C. to −3° C., over 22 minutes. Five minutes later, the contents of the reactor transformed to a light yellow colored slurry that was indicative of a triethylamine hydrobromide product. HPLC analysis of the triethylamine hydrobromide product revealed 24 components with every component present having a different retention time than those observed in the HPLC analysis of the dicyclopentadiene polyphenol. Twenty-seven minutes after the triethylamine addition, during which the reactor contents were maintained at a temperature of −7° C. to −2° C., the reactor contents were added to a beaker of deionized water (400 milliliters) and dichloromethane (250 milliliters). The beaker contents were stirred for 2 minutes and then allowed to separate in a separatory funnel from which the dichloromethane layer was recovered and the aqueous layer was discarded. The dichloromethane layer was added back into the separatory funnel and extracted with fresh deionized water (400 milliliters initially, 250 milliliters thereafter) three additional times to provide a hazy dichloromethane solution. The hazy dichloromethane solution was dried over granular anhydrous sodium sulfate (25 g) to provide a clear solution that was then passed through a bed of anhydrous sodium sulfate (100 g) supported on a 400 milliliter, medium fritted glass funnel attached to a side arm vacuum flask to provide a clear, light yellow colored filtrate. The filtrate was rotary evaporated using a maximum oil bath temperature of 55° C. Additional rotary evaporation was performed at 75° C. until a vacuum of 0.4 mm Hg was reached to provide a solid powder. The solid powder was then placed in the vacuum oven heated to 75° C. for 16 hours to provide 23.14 g of dicyclopentiadiene polycyanate, which was observed to be a light yellow solid. FTIR analysis of a potassium bromide pellet of the dicyclopentadiene polycyanate provided there was no hydroxyl group absorbance while a strong cyanate group absorbance at 2265.2 and 2235.4 $cm^{-1}$ was observed. HPLC analysis indicated 16 components with 3 predominant components comprising 27.9, 24.0 and 31.8 area % respectively.

Comparative Example A

Composition of Dicyclopentadiene Polycyanate

Differential scanning calorimetry (DSC) analysis of Comparative Example A, a composition of dicyclopentadiene polycyanate as prepared above, (6.6 mg) was performed with a heating rate of 7° C. per minute from 25° C. to 350° C. under nitrogen stream (35 cc/m). No melt endotherm was detected. A single exotherm attributed to cyclotrimerization was detected with a 162.6° C. onset, a 262.3° C. midpoint, and a 304.6° C. end. A cure enthalpy of 164.4 joules per gram, as seen in Table 1A, was determined. DSC analysis of the resultant homopolytriazine of dicyclopentadiene polycyanate indicated minor further exothermicity commencing at 271.1° C. A subsequent DSC analysis shifted the onset of minor exothermicity to 307.1° C. The homopolytriazine recovered from the DSC analysis was a transparent; amber colored, rigid solid.

Comparative Example B

Composition of Bisphenol A Dicyanate

DSC analysis of Comparative Example B, a composition of bisphenol A dicyanate, (10.1 milligrams) was performed with a heating rate of 7° C. per minute from 25° C. to 350° C. under nitrogen stream (35 cc/m). There was a single sharp melt endotherm with a 83.0° C. midpoint accompanied. A melt enthalpy of 98.7 joules per gram was determined. A single exotherm attributed to cyclotrimerization was detected with a 244.1° C. onset, a 320.7° C. midpoint, and a 352.6° C. end. A cure enthalpy of 588.9 joules per gram, as seen in Table 1A, was determined. DSC analysis of the resultant homopolytriazine of bisphenol A dicyanate indicated minor further exothermicity commencing at 319.9° C., with a noted gradual exothermic shift starting at 150° C. A subsequent DSC analysis provided exothermicity commencing at 209.8° C. with a more pronounced exothermic shift commencing at 320.4° C. The homopolytriazine recovered from the DSC analysis was a transparent, light amber colored, rigid solid.

Comparative Example C

Product Obtained by Curing Comparative Example A

Comparative Example A, a composition including dicyclopentiadiene polycyanate as prepared above, (0.5 g) was placed in an aluminum container and then into a 100° C. oven for one hour. Then the container and contents were transferred to a 150° C. oven for one hour. Comparative Example A was a homogeneous liquid after 23 minutes in the 150° C. oven. The liquid was placed in a 200° C. oven for 1 hour, then a 250° C. oven for 1 hour and finally a 300° C. oven for 1 hour followed by slow cooling to 22° C. to provide Comparative Example C, a product obtained by curing a composition including dicyclopentadiene polycyanate. The product was a transparent, amber colored, rigid solid. DSC analysis of the product (18.9 milligrams) indicated a glass transition at a temperature of 295.70° C., as seen in Table 2A.

Comparative Example D

Product Obtained by Curing Comparative Example B

The process of Comparative Example C was repeated, except that Comparative Example B (0.5 gram) was substituted for Comparative Example A. Comparative Example B was a homogeneous liquid while in the 100° C. oven. The heating and slow cooling, as described above, provided Comparative Example D, a product obtained by curing a composition including of bisphenol A dicyanate. The product was a transparent, yellow colored, rigid solid. DSC analysis of the product (19.5 milligrams) provided a glass transition at a temperature of 275.70° C., as seen in Table 2A.

Example 1

Synthesis of Vinylbenzyl Ether of Polycyclopentadiene Polyphenol

Dicyclopentadiene polyphenol was prepared as above using isomeric dicyclopentadienes (97.3 area % (GC)) and monoaldehyde isomers (1.2 area % (GC)) and higher molecular weight byproducts.

Dicyclopentadiene polyphenol (133.16 g, nominally 1.0 hydroxyl equivalent), anhydrous methanol (264 g), and 2,6-di-tertiary-butyl-4-methylphenol (0.1343 g) were added to a 5 liter glass three neck round bottom reactor. The reactor included a chilled (0° C.) condenser, a thermometer, both affixed to the reactor via a Claisen adaptor, an addition funnel capped with an overhead nitrogen inlet, a glass stirring shaft with a Teflon™ stirrer blade coupled to a variable speed motor, and a thermostatically controlled heating mantle. Overhead nitrogen flow (1 liter per min) was established and the contents of the reactor were stirred for 62 minutes to provide an amber colored solution. After three minutes, lithium hydroxide powder (14.3 grams, 0.597 mole) was added to the contents of the reactor which resulted in a 39° C. exotherm and color change of the solution to a red amber colored solution. A fan was used to cool the reactor exterior which reached a maximum temperature of 41° C. four minutes after the addition of the lithium hydroxide. Fifteen minutes after the lithium hydroxide addition, the exterior of the reactor was at a temperature of 30° C. and further lithium hydroxide (14.3 grams, 0.597 mole) was added to the contents of the reactor to provide a maximum exotherm of 37° C. After another fifteen minutes, further lithium hydroxide (14.3 grams, 0.597 mole) was added to the contents of the reactor with no resultant exotherm. Then the contents of the reactor were heated to 55° C. over 35 minutes and vinylbenzyl chloride (55.94 grams, 0.3664 mole) was added to the contents of the reactor over 13 minutes via the addition funnel. Fifty-eight minutes after the inception of the initial vinylbenzyl chloride addition, further vinylbenzyl chloride (112.19 grams, 0.7349 mole) was added to the contents of the reactor over 60 minutes to provide an orange colored slurry having white suspended particulates. After 3.5 hours anhydrous methanol (264 grams) was added to the contents of the reactor to reduce viscosity. HPLC analysis indicated that 16.2 hours after the inception of the initial vinylbenzyl chloride addition that the vinylbenzyl chloride added to the reactor had been completely consumed. At this time, further methanol (278 grams) was added to the contents of the reactor, followed by further vinylbenzyl chloride (50.84 grams, 0.3330 mole) added over 35 minutes. Further vinylbenzyl chloride (50.84 grams, 0.3330 mole) was added to the contents of the reactor over 35 minutes 24.8 hours after the inception of the initial vinylbenzyl chloride addition. Further vinylbenzyl chloride (25.42 grams, 0.1665 mole) was added to the contents of the reactor over 16 minutes 48 hours after the inception of the initial vinylbenzyl chloride addition. The contents of the reactor were maintained at 55° C. and stirred for 62.8 hours after the inception of the initial vinylbenzyl chloride addition, after which the contents of the reactor were cooled to a temperature of 25° C. to provide a cloudy light yellow colored liquid and solids. The cloudy light yellow colored liquid was decanted and discarded. Methanol (1 liter) was added to the solids and the contents of the reactor were stirred under a nitrogen atmosphere for 110 minutes. Then the contents of the reactor were allowed settle and the methanol phase was decanted and discarded. Further methanol (1 liter) was added to the contents of the reactor, which were stirred under a nitrogen atmosphere for 75 minutes. Then the contents of the reactor were allowed settle and the methanol phase was decanted and discarded. Further methanol (1 liter) was added to the contents of the reactor, which were stirred under a nitrogen atmosphere for 18 hours. Then the contents of the reactor were allowed settle and the methanol phase was decanted and discarded. Dichloromethane (1 liter) was added to the contents of the reactor, which were stirred under a nitrogen atmosphere for 2.5 hours. The contents of the reactor divided and equally placed into two 750 milliliter polypropylene bottles and centrifuged for 30 minutes at 2300 rotations per minute (RPM). A cloudy, light amber colored liquid which separated was recovered from the bottles by decantation through filter paper. The remaining solids were combined with further dichloromethane and extracted by placing in a mechanical shaker for 30 minutes. The resultant slurry was centrifuged for one hour at 2300 RPM followed by decantation of the separated liquid through filter paper. The combined decants were filtered through a bed of diatomaceous earth packed one inch deep on a 600 milliliter medium flitted glass funnel. Methanol (2.5 liters) was added to the transparent filtrate while stirring with a spatula in a 4 liter glass beaker. A yellow gummy solid including the vinylbenzyl ethers of dicyclopentadiene polyphenol precipitated and was recovered after decantation and dried-in a vacuum oven at a temperature of 75° C. to a constant weight of 116.90 grams. FTIR analysis of a potassium bromide pellet of the vinylbenzyl ether of dicyclopentadiene polyphenol indicated complete disappearance of hydroxyl group absorbance; appearance of aromatic ring absorbance at 1507.15 (s), 1582.17 (m) and 1607.10 (m) $cm^{-1}$; =CH vibration in conjugation with the aromatic ring at 1628.59 (m) $cm^{-1}$; absorbances within the region for aromatic C—H bending vibration where meta substitution provides 3 adjacent hydrogens at 751.71 (m) and 794.16 (m) $cm^{-1}$; an absorbance within the region for aromatic C—H bending vibration where para substitution provides 2 adjacent hydrogens at 826.92 (s) $cm^{-1}$; and C—O stretching absorbance at 1112.20 (m) $cm^{-1}$.

Example 2

Thermosettable Composition Including Vinylbenzyl Ethers of Dicyclopentadiene Polyphenol Differential scanning calorimetry (DSC) analysis of two portions of Example 2 (Sample 1 and Sample 2), a thermosettable composition including the vinylbenzyl ethers of dicyclopentadiene polyphenol as prepared above, (8.9 and 9.9 milligrams) was performed with a heating rate of 7° C. per minute from 25° C. to 425° C. under nitrogen stream (35 cc/m). No melt endotherm was detected. A pair of exotherms attributed to homopolymerization were detected. At the end of the second exotherm (400.43° C. and 403.40° C., respectively for the two samples, 401.92° C. average) a sharp exothermic decomposition occurred. Respective cure enthalpies of Example 2 (Sample 1 and Sample 2) 72.22 and 93.53 joules per gram, as seen in Table 1B, were determined.

Example 3

Product Obtained by Curing a Thermosettable Composition Including Vinylbenzyl Ethers of Dicyclopentadiene Polyphenol A thermosettable composition including the vinylbenzyl ethers of dicyclopentadiene polyphenol as prepared above, (0.5 gram) was placed in an aluminum dish and placed into a 100° C. oven for one hour to provide a product that was observed to be a transparent, light yellow colored casting. Then, the dish was placed in a 150° C. oven for one hour, a 200° C. oven for one hour, and a 250° C. for one hour followed by slow cooling to 22° C. to provide a product obtained by curing the thermosettable composition including vinylbenzyl ethers of dicyclopentadiene polyphenol that was observed to be a transparent, light amber colored, rigid solid. DSC analysis of this product (26.40 milligrams) was performed with a heating rate of 7° C. per minute from 25° C. to 400° C. under nitrogen stream (35 cc/m) and indicated a glass transition at a temperature of 317.04° C. after the fourth scan, as seen in Table 2B.

Example 4

Thermosettable Composition Including Vinylbenzyl Ethers of Dicyclopentadiene Polyphenol and Comonomer (Bisphenol A Dicyanate, 57.15 wt %)

Vinylbenzyl ether of dicyclopentadiene polyphenol, as prepared above, (0.0980 gram, 42.85 weight %) and bisphenol A dicyanate (0.1307 gram, 57.15 weight %) were added to a glass vial and ground with a spatula to provide Example 4, a thermosettable composition observed to be a homogeneous powder.

Example 5

Product Obtained by Curing Thermosettable Composition Including Vinylbenzyl Ethers of Dicyclopentadiene Polyphenol and Comonomer (Bisphenol A Dicyanate, 57.15 wt %)

DSC analysis of Example 4 (8.4 milligrams) was performed with a heating rate of 7° C. per minute from 25° C. to 350° C. under nitrogen stream (35 cc/m). A melt endotherm was detected with an onset of 51.80° C., a minimum of 79.74° C., an end of 86.64° C. and a melt enthalpy of 52.43 joules/gram. A single exotherm attributed to copolymerization was detected with an onset of 197.36° C., a maximum of 266.86° C., an end of 331.73° C. A cure enthalpy of 313.3 joules per gram, as seen in Table 1B, was determined. A subsequent DSC scan on Example 5, a product obtained by curing the thermosettable composition that employed the above conditions indicated a glass transition temperature of 294.79° C., as seen in Table 2B.

Example 6

Thermosettable Composition Including Vinylbenzyl Ethers of Dicyclopentadiene Polyphenol and Comonomer (Bisphenol A Dicyanate, 50 wt %)

Vinylbenzyl ether of dicyclopentadiene polyphenol, as prepared above, (0.1435 gram, 50.00 weight %) and bisphenol A dicyanate (0.1435 gram, 50.00 weight %) were added to a glass vial and ground together with a spatula to provide Example 6, a thermosettable composition observed to be a homogeneous powder.

Example 7

Product Obtained by Curing Thermosettable Composition Including Vinylbenzyl Ethers of Dicyclopentadiene Polyphenol and Comonomer (Bisphenol A Dicyanate, 50 wt %)

DSC analysis of Example 6 (10.7 milligrams) was performed as above. A melt endotherm was detected with an onset of 50.97° C., a minimum of 81.16° C., an end of 89.95° C. and a melt enthalpy of 42.01 joules/gram. A single exotherm attributed to copolymerization was detected with an onset of 184.51° C., a maximum of 262.83° C., an end of 327.17° C. A cure enthalpy of 245.5 joules per gram, as seen in Table 1B, was determined. A subsequent DSC scan on Example 7, a product obtained by curing the thermosettable composition using the aforementioned conditions indicated a glass transition temperature of 297.75° C., as seen in Table 2B.

Example 8

Thermosettable Composition Including Vinylbenzyl Ethers of Dicyclopentadiene Polyphenol and Comonomer (Bisphenol A Dicyanate, 39.99 wt %)

Vinylbenzyl ether of dicyclopentadiene polyphenol, as prepared above, (0.1811 gram, 60.01 weight %) and bisphenol A dicyanate (0.1207 gram, 39.99 weight %) were added to a glass vial and ground together with a spatula to provide Example 8, a thermosettable composition observed to be a homogeneous powder.

Example 9

Product Obtained by Curing Thermosettable Composition Including Vinylbenzyl Ethers of Dicyclopentadiene Polyphenol and Comonomer (Bisphenol A Dicyanate, 39.99 wt %)

DSC analysis of Example 8 (9.30 milligrams) was performed as above. A melt endotherm was detected with an onset of 52.22° C., a minimum of 80.73° C., an end of 89.13° C. and a melt enthalpy of 38.02 joules/gram. A single exotherm attributed to copolymerization was detected with an onset of 178.70° C., a maximum of 259.12° C., an end of 320.12° C. A cure enthalpy of 224.2 joules per gram, as seen in Table 1B, was determined. A subsequent DSC scan on Example 9, a product obtained by curing the thermosettable composition using the aforementioned conditions indicated a glass transition temperature of 292.07° C., as seen in Table 2B.

Example 10

Thermosettable Composition Including Vinylbenzyl Ethers of Dicyclopentadiene Polyphenol and Comonomer (Polycyanate of Dicyclopentadiene Polyphenol, 50 wt %)

Vinylbenzyl ether of dicyclopentadiene polyphenol, as prepared above, (0.1824 gram, 50.00 weight %) and polycyanate of dicyclopentadiene polyphenol, as prepared above, (0.1824 gram, 50.00 weight %) were added to a glass vial and ground together with a spatula to provide Example 10, a thermosettable composition observed to be a homogeneous powder.

Example 11

Product Obtained by Curing Thermosettable Composition Including Vinylbenzyl Ethers of Dicyclopentadiene Polyphenol and Comonomer (Polycyanate of Dicyclopentadiene Polyphenole, 50 wt %)

DSC analysis of Example 10 (8.10 milligrams) was performed as above. No melt endotherm was detected. A single exotherm attributed to copolymerization was detected with an onset of 177.87° C., a maximum of 235.95° C., an end of 295.23° C. A cure enthalpy of 100.8 joules per gram, as seen in Table 1B, was determined. A subsequent DSC scan on Example 11 (Sample 1), a product obtained by curing the thermosettable composition using the aforementioned conditions revealed a glass transition temperature of 294.80° C., as seen in Table 2B. A repeat of the aforementioned DSC analysis including Example 11 (Sample 2) (8.60 milligram sample) indicated a glass transition temperature of 295.37° C., as seen in Table 2B.

TABLE 1A

| Comparative Example | Cure Enthalpy (joules/gram) |
|---|---|
| Comparative Example A | 164.4 |
| Comparative Example B | 588.9 |

TABLE 1B

| Example | Cure Enthalpy (joules/gram) |
|---|---|
| Example 2 (Sample 1) | 72.2 |
| Example 2 (Sample 2) | 93.5 |
| Example 4 | 313.3 |
| Example 6 | 245.5 |
| Example 8 | 224.2 |
| Example 10 | 100.8 |

The data in Tables 1A-1B shows that Example 2, both Sample 1 and Sample 2, the thermosettable compositions including vinylbenzyl ethers of dicyclopentadiene polyphenol, have a lower cure enthalpy than either Comparative Example A, the composition of dicyclopentadiene polycyanate, or Comparative Example B, the composition of bisphenol A dicyanate.

The data in Tables 1A-1B further shows that each of Examples 4, 6, 8, and 10, each being a thermosettable composition including vinylbenzyl ethers of dicyclopentadiene polyphenol and a comonomer, have a lower cure enthalpy than Comparative Example B.

TABLE 2A

| Comparative Example | Glass Transition Temperature (° C.) |
|---|---|
| Comparative Example C | 295.70 |
| Comparative Example D | 275.70 |

TABLE 2B

| Example | Glass Transition Temperature (° C.) |
|---|---|
| Example 3 | 317.04 |
| Example 5 | 294.79 |
| Example 7 | 297.75 |
| Example 9 | 292.07 |
| Example 11 (Sample 1) | 294.80 |
| Example 11 (Sample 2) | 295.37 |

The data in Tables 2A-2B shows that Example 3, the product obtained by curing a thermosettable composition including vinylbenzyl ethers of dicyclopentadiene polyphenol, has a greater glass transition temperature than either Comparative Example C, a product obtained by curing Comparative Example A, or Comparative Example D, a product obtained by curing Comparative Example B.

The data in Tables 2A-2B further shows that each of Examples 5, 7, 9, and 11 (Sample 1 and Sample 2), each being a product obtained by curing a thermosettable composition including vinylbenzyl ethers of dicyclopentadiene polyphenol and a comonomer, have greater glass transition temperature than Comparative Example D.

What is claimed:

1. A vinylbenzyl ether of polycyclopentadiene polyphenol of Formula I:

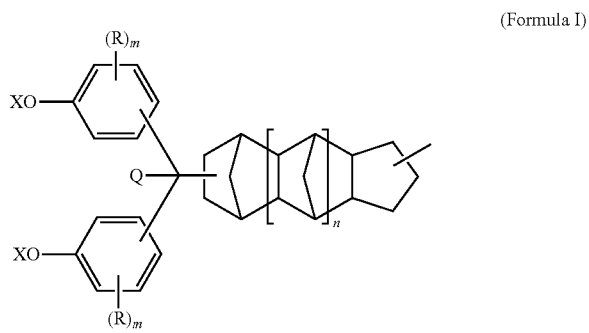

(Formula I)

-continued

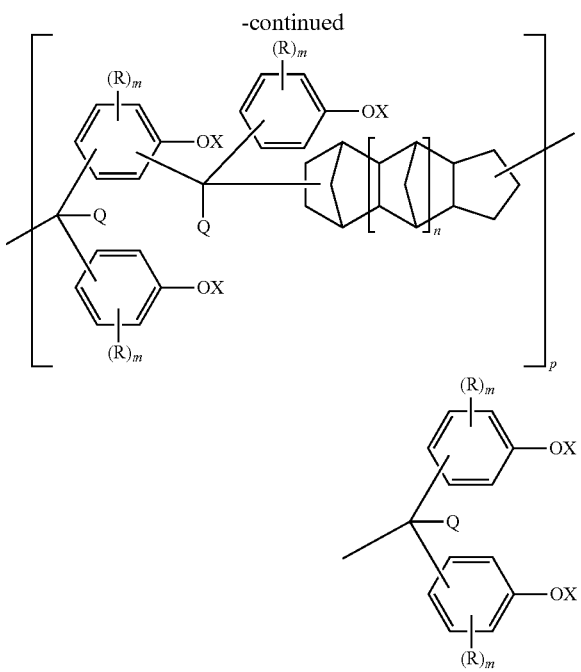

in which each n independently has a value from zero to 20; each m independently has a value of zero to 3; p has a value of zero to 20; each R is independently a halogen, a nitrile group, a nitro group, an alkyl group, an alkoxy group, an alkenyl group, or an alkenyloxy group, where the alkyl group, the alkoxy group, the alkenyl group, and the alkenyloxy group each independently contain 1 to 6 carbon atoms; each Q is independently hydrogen or an alkyl group containing 1 to 6 carbon atoms; and each X is a group of Formula II

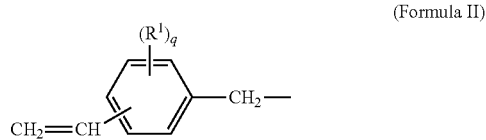
(Formula II)

in which each $R^1$ is independently a halogen, a nitrile group, a nitro group, an alkyl group, an alkoxy group, an alkenyl group, or an alkenyloxy group, where the alkyl group, the alkoxy group, the alkenyl group, and the alkenyloxy group each independently contain 1 to 6 carbon atoms; and each q independently has a value of zero to 4.

2. The vinylbenzyl ether of polycyclopentadiene polyphenol of claim 1, wherein each R halogen and each $R^1$ halogen is independently selected from the group of fluorine, chlorine, and bromine.

3. The vinylbenzyl ether of polycyclopentadiene polyphenol of claim 1, wherein each n independently has a value from zero to 8.

4. The vinylbenzyl ether of polycyclopentadiene polyphenol of claim 1, wherein p has a value from zero to 1.

5. The vinylbenzyl ether of polycyclopentadiene polyphenol of claim 1, wherein each alkyl group independently contains 1 to 2 carbon atoms.

6. The vinylbenzyl ether of polycyclopentadiene polyphenol of claim 1, wherein each alkoxy group independently contains 1 to 2 carbon atoms.

7. The vinylbenzyl ether of polycyclopentadiene polyphenol of claim 1, wherein m is zero.

8. A thermosettable composition comprising the vinylbenzyl ether of polycyclopentadiene polyphenol as in claim 1.

9. The thermosettable composition of claim 8, further comprising a comonomer selected from the group consisting of polymaleimides, polycyanates, polycyanamides, epoxy compounds, compounds containing one or more polymerizable ethylenically unsaturated group(s), and combinations thereof.

10. The thermosettable composition of claim 9, wherein the comonomer is from 5 weight percent to 90 weight percent of a total weight percent the monomers included in the thermosettable composition.

11. A product obtainable by curing the thermosettable composition of claim 8.

12. The product as in claim 11, where the product comprises a B-staged product.

13. The product of claim 11, where the product comprises an infusible polymer network.

* * * * *

UNITED STATES PATENT AND TRADEMARK OFFICE
CERTIFICATE OF CORRECTION

PATENT NO. : 8,664,341 B2
APPLICATION NO. : 13/643656
DATED : March 4, 2014
INVENTOR(S) : Robert E. Hefner, Jr.

It is certified that error appears in the above-identified patent and that said Letters Patent is hereby corrected as shown below:

On the Title Page (Page 1):

Assignee "Dow Global Technologies, LLC" should read "Dow Global Technologies LLC"

Signed and Sealed this
Fifth Day of May, 2015

Michelle K. Lee
*Director of the United States Patent and Trademark Office*